United States Patent
Jones

(10) Patent No.: US 6,258,980 B1
(45) Date of Patent: *Jul. 10, 2001

(54) PRODUCTION OF METAL SALTS

(75) Inventor: David Anthony Jones, Warrington (GB)

(73) Assignee: Contracts Chemicals Ltd., Prescot (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/266,388

(22) Filed: Jun. 27, 1994

(30) Foreign Application Priority Data

Jun. 30, 1993 (GB) .................................................. 9313444

(51) Int. Cl.$^7$ ..................................................... C07C 51/42
(52) U.S. Cl. ........................... 562/485; 562/486; 562/593; 562/600; 562/606; 562/607; 562/608; 562/609
(58) Field of Search ..................................... 562/606, 607, 562/608, 609, 485, 486, 593, 600

(56) References Cited

U.S. PATENT DOCUMENTS

| | | | | |
|---|---|---|---|---|
| 2,895,990 | * | 7/1959 | Larrison et al. | 562/606 |
| 3,719,654 | | 3/1973 | Stone | 260/97.5 |
| 4,374,777 | | 2/1983 | Henry | 260/414 |
| 4,558,070 | * | 12/1985 | Bauer et al. | 562/606 |

FOREIGN PATENT DOCUMENTS

1173814   10/1969   (GB) .

* cited by examiner

Primary Examiner—Dwayne C. Jones
(74) Attorney, Agent, or Firm—Smith, Gambrell & Russell

(57) ABSTRACT

There is described a process for the production of a substantially anhydrous salt of an organic acid which comprises reacting a basic compound of a metal with the appropriate organic acid, removing a substantial proportion of water present so as to produce the salt or its hydrate as a liquid phase and then dissolving the liquid phase in a non-aqueous solvent.

6 Claims, No Drawings

PRODUCTION OF METAL SALTS

The present invention relates to the production of metal salts of organic acids. More particularly it relates to the production of such salts and their dissolution in a non-aqueous solvent.

BACKGROUND OF INVENTION

The production of metal salts of organic acids by the reaction of a basic compound of the metal with the appropriate acid is known. However, such a process usually produces water as a function of the acid-base neutralization reaction which occurs. This water is usually undesirable and has to be removed by physical means to yield the anhydrous salt which is normally required. Many techniques have been proposed for removing this water, for example, distillation. However, high temperatures or vacuum are needed to make this process efficient, which is often impractical because the salts formed are normally high melting solids, and unless special equipment is utilized do not lend themselves to easy or effective processing. Indeed, in some cases, conventional methods for removal of water by the use of heat, even with reduced pressure, lead to a material from which removal of further water (free or water of hydration) is difficult by conventional heating methods.

SUMMARY OF INVENTION

According to the present invention there is provided a process for the production of substantially anhydrous salts of organic acids which comprises reacting a basic compound of the metal with the appropriate organic acid, removing a substantial proportion of water present so as to produce the salt or its hydrate as a liquid phase; such liquid phase is then dissolved in a non aqueous solvent.

DETAILED EMBODIMENT OF THE INVENTION

The water present arises not only from water which may have been present as the solvent for an aqueous solution of the basic compound used in the reaction but may also be produced by the reaction. A substantial proportion of such water present may be removed e.g. to a level of about 0.05% to 5% based on the weight of the product, preferably about 0.5 to 1.5%, most preferably about 1% by conventional distillation, usually at atmospheric pressure, utilizing temperatures up to the order of 350° C. The water removal is preferably carried out in two stages, the first one removing part of the water e.g. to a level of about 5 to 20% followed by a second removal down to the final level required.

The present invention has particular applicability to the production of those metal salts which as such, or particularly in a hydrate form, have a melting point of less than 250° C. For such salts (or their hydrates), the distillation to remove a substantial proportion of the water can be conducted, not only in its earlier stages but also in its latter stages wherein effectively the liquid salt or liquid hydrate thereof is being treated, with stirring to assist removal of further water.

The metal salt resulting from the distillation may be cooled to some extent, but while still at elevated temperature and in a liquid phase, is then dissolved in the desired non aqueous solvent. The water content of the hot liquid metal salt being dissolved in the solvent is usually less than 5%. It can be substantially lower so that the water content of the solution of the metal salt in the non-aqueous solvent can be as low as of the order of 1% and can be considered as substantially anhydrous.

The metal is for example an alkali metal i.e. lithium, sodium, potassium, rubidium or cerium or an alkaline earth metal i.e. beryllium, magnesium, calcium, strontium or barium, and the basic compound of the metal may be, for example, a hydroxide or carbonate of an alkali metal or an alkaline earth metal and the organic acid may be, for example, one derived from an aliphatic hydrocarbon e.g. a carboxylic acid e.g. monocarboxylic acid, a dicarboxylic acid or a polycarboxilic acid, typically containing from about 2 to about 20 carbon atoms. If an alkali metal hydroxide is employed, it may be, for example, a commercially supplied material of 50% strength in water. Its use in such form would of course lead to the formation of a comparatively dilute solution of the metal salt in water.

The metal salt is preferably a sodium or potassium salt. The acid is preferably 2-ethyl hexanoic acid. The present invention is of particular applicability to the reaction of potassium hydroxide or carbonate with an organic acid such as, for example, 2-ethyl hexanoic acid leading to the formation of an aqueous solution or slurry of potassium 2-ethyl hexanoic.

The removal of water from the solution or slurry of the metal salt is undertaken firstly, as referred to above, by conventional distillation at atmospheric pressure, usually with agitation, at up to about 350° C. Preferably the temperature employed is in the range of 100° C. to 350° C., more preferably 100° C. to 250° C. In practice, the temperature rises as the amount of water present diminishes. In the region of the upper temperature of the range employed, the last traces of water which might remain can be substantially removed by applying a slight vacuum to the system. Also in that latter stage, it is preferred to maintain the upper limit of the temperature in the range of 200° C. to 250° C. in order to avoid charring or other detrimental thermal processes.

The molten metal salt, with the desired low water content, is dissolved while still hot but usually at a temperature lower than the upper limit of the temperature ranges referred to above, in a non-aqueous solvent in which the metal salt has reasonable solubility by slow addition. The addition is preferably conductional so that refluxing of the solvent cools the solution which forms. Classes of useful solvents include alcohols, for example isopropanol, esters, for example ethyl acetate, and ethers, for example tetrahydrofuran.

If the salt produced is potassium 2-ethylhexanoate, the concentration of it in the solution is usually in the range of 10 to 90%, with a water content of less than 5%, usually of the order of 1%.

The process of the present invention may be carried out using conventional equipment.

Once formulated one use of this product, either as a solution or as an anhydrous salt, is as a source of metal ions e.g. in the pharmaceutical industry, specifically in antibiotics production.

The present invention will now be described with reference to, but in no manner limited to, the following Examples.

EXAMPLE 1

To 2-ethyehexanoic acid (144.2g, 1.0 mole) was added with stirring, a commercial, 50% aqueous solution of potassium hydroxide (112.2g, 1.0 mole) over 2h. The temperature of the reaction was allowed to exotherm from ambient to 45° C. during the addition and cooling applied to maintain this level (±5° C.). The resulting, clear, colorless solution was then stirred for a further 3h and then allowed to stand overnight.

The water (theoretical =74.1 g) was then removed with continuous stirring, by distillation under atmospheric pressure up to 308° C., as tabulated below: on Volume of

| Distillation Temperature (° C.) | Volume of Water Removed (ml) |
| --- | --- |
| 120 | 7.5 |
| 122 | 15.0 |
| 125 | 22.5 |
| 130 | 30.0 |
| 148 | 50.0 |
| 162 | 60.0 |
| 198 | 70.0 |
| 250 | 71.0 |
| 308 | 72.0 |

The resultant yellow liquid was then cooled to above 160° C. and isopropanol (300ml) added slowly. This then gave a clear, amber colored solution of potassium 2-ethylhexanoate in isopropanol with a salt content of 43% and water at 1.3%

EXAMPLE 2

The procedure of Example 1 was followed to produce the aqueous solution of potassium 2-ethyhexanoate.

On removal of the water again with continuous agitation, by atmospheric distillation, the following profile was obtained:

| Distillation Temperature (° C.) | Volume of Water Removed (ml) |
| --- | --- |
| 125 | 20 |
| 138 | 40 |
| 165 | 60 |
| 215 | 69 |

Once at 215° C., partial vacuum was applied for a short period to remove substantially the last traces of water. The reaction was then allowed to cool to 190° C. and isopropanol (300 ml) added slowly, cooling the resulting solution further through reflux. There resulted a clear, amber liquid containing 41.3% salt and with a water content of 0.8%.

EXAMPLE 3

A solution of potassium hydroxide (375 Kg at 90% purity, 6.0 Kmole) in water (500 Kg) was prepared and then added to 2-ethylhexanoic acid (866 Kg, 6.0 Kmole) as described in Example 1.

The water was removed by distillation with continuous stirring up to 240° C. At this point the level of water remaining in the molten salt was at 1.2%. After cooling slightly, isopropanol (1620 Kg) was added slowly, and stirring continued to dissolve the salt, during this period the temperature of the vessel contents dropped to 70° C. This then produced a clear, amber liquid assaying at 40.6% with a water content of 1% (2570 Kg. 91%).

I claim:

1. A process for the production of a substantially anhydrous potassium 2-ethyl hexanoate, having a water content of 0.05% to 5% based on the weight of the product, which comprises reacting a basic compound of potassium with 2 ethyl hexanoic acid, and removing a substantial proportion of water present to a content of 0.05% to 5% based on the weight of the product so as to produce the salt or its hydrate as a liquid phase.

2. A process as claimed in claim 1, in which the substantial proportion of water is removed by distillation.

3. A process as claimed in claim 1, in which the basic compound of potassium is potassium hydroxide or potassium carbonate.

4. A process as claimed in claim 1, in which the liquid phase obtained is then dissolved in a non-aqueous solvent.

5. A process as claimed in claim 4, in which the non-aqueous solvent is an alcohol or an ester.

6. A process as claimed in claim 4, in which the solvent is isopropanol or ethyl acetate.

* * * * *